(12) United States Patent
Heo

(10) Patent No.: US 8,591,232 B2
(45) Date of Patent: Nov. 26, 2013

(54) DRILL FOR SINUS MEMBRANE LIFT

(76) Inventor: Young Ku Heo, Seoul (KR)

( * ) Notice: Subject to any disclaimer, the term of this patent is extended or adjusted under 35 U.S.C. 154(b) by 32 days.

(21) Appl. No.: 12/679,659

(22) PCT Filed: Jul. 21, 2008

(86) PCT No.: PCT/KR2008/004242
§ 371 (c)(1),
(2), (4) Date: Mar. 23, 2010

(87) PCT Pub. No.: WO2009/099267
PCT Pub. Date: Aug. 13, 2009

(65) Prior Publication Data
US 2010/0196844 A1 Aug. 5, 2010

(30) Foreign Application Priority Data
Feb. 4, 2008 (KR) .......... 10-2008-0011241

(51) Int. Cl.
*A61C 3/02* (2006.01)
(52) U.S. Cl.
USPC ............................................. 433/165
(58) Field of Classification Search
USPC .............. 433/72, 75, 102, 165; 606/80, 96, 606/177–180, 81; 24/456, 535, 536, 569; 408/199, 227, 229, 202; 82/160
See application file for complete search history.

(56) References Cited

U.S. PATENT DOCUMENTS

| | | | | |
|---|---|---|---|---|
| 569,896 A * | 10/1896 | Van Cauwenberg | ......... | 408/202 |
| 679,693 A * | 7/1901 | Burkhart | ....................... | 408/191 |
| 866,963 A * | 9/1907 | Rauhe | ........................... | 433/165 |
| 1,022,838 A * | 4/1912 | Funk | ............................... | 433/102 |
| 2,121,193 A * | 6/1938 | Hanicke | ......................... | 606/65 |
| 3,633,583 A * | 1/1972 | Fishbein | ......................... | 606/81 |
| 4,019,254 A * | 4/1977 | Malmin | ........................ | 433/102 |
| 4,019,827 A * | 4/1977 | Christianson et al. | ........ | 408/202 |
| 4,131,116 A * | 12/1978 | Hedrick | ......................... | 606/81 |
| 4,443,193 A * | 4/1984 | Roane | ........................... | 433/102 |
| 5,066,174 A * | 11/1991 | Smith | ............................. | 408/79 |
| 5,078,605 A * | 1/1992 | Sutter et al. | ................... | 433/165 |
| 5,941,706 A * | 8/1999 | Ura | ................................. | 433/165 |
| 6,579,092 B1 * | 6/2003 | Senia et al. | .................... | 433/102 |
| 6,637,989 B1 * | 10/2003 | Moore | ........................... | 408/119 |
| 2006/0008332 A1 * | 1/2006 | Greenberg et al. | ........... | 408/202 |
| 2006/0015110 A1 * | 1/2006 | Pepper | ............................ | 606/80 |
| 2007/0088361 A1 * | 4/2007 | Ho | ................................... | 606/80 |
| 2007/0099150 A1 * | 5/2007 | Muller et al. | .................. | 433/165 |
| 2008/0113316 A1 * | 5/2008 | Menke | ........................... | 433/174 |
| 2009/0259227 A1 * | 10/2009 | Ahn | ................................ | 606/80 |

* cited by examiner

*Primary Examiner* — Yogesh Patel
(74) *Attorney, Agent, or Firm* — Park & Associates IP Law, P.C.

(57) ABSTRACT

A drill for sinus membrane lift includes a contact surface for coming in face contact with sinus membrane, the contact surface having a curved periphery, and a bone-maintaining area connected to the contact surface for storing and discharging drilled bone fragments. The bone-maintaining area includes a first inside wall and a second inside wall connected to the first inside wall, the first inside wall oriented in a drilling direction, and the second inside wall opposite the first inside wall. The first inside wall has a drilling surface and is formed higher than the second inside wall so that the drilling surface is exposed in the drilling direction. The front end of the head comes into face contact with the sinus membrane at a wide area to prevent the sinus membrane from being torn or damaged even if the head completely penetrates the maxilla and contacts the sinus membrane.

10 Claims, 36 Drawing Sheets

DRILL FOR SINUS MEMBRANE LIFT

This application is a national stage application of PCT/KR2008/004242 filed on Jul. 21, 2008, which claims priority of Korean patent application number 10-2008-0011241 filed on Feb. 4, 2008. The disclosure of each of the foregoing applications is incorporated herein by reference in its entirety.

TECHNICAL FIELD

The present invention relates to a drill used in a procedure for installing a surgical implant, and more particularly, to a drill for sinus membrane lift, which is designed to safely and precisely drill the maxilla or the upper jawbone, thereby ensuring safety and convenience in the procedure.

BACKGROUND ART

In general, a dental implant is an artificial tooth root that replaces a missing tooth of a patient. The dental implant is installed and incorporated to a toothless site of the alveolar bone and then is fixed to the alveolar bone in order to replace a missing tooth root and recover the original function of the tooth. Here, the dental implant is made of a biocompatible alloy of for example titanium.

A dental implant procedure generally involves several surgeries such as incising and peeling the soft tissue and drilling the bone for installation of the implant, installing the implant, and constructing an upper prosthesis. The surgeries for incising and peeling the soft tissue are not significantly different from the principle of a typical periodontal surgery. The surgery of drilling the bone generally includes a process of drilling the cortical bone and drilling the cancellous bone. The bone drilling surgery involves, according to the basic principles thereof, trimming the bone near an implant site, marking the implant site, and drilling a small hole in the cortical bone, followed by gradually enlarging the hole up to a diameter substantially the same as or slightly smaller than that of an implant to be installed.

Then, the implant is installed after the alveolar bone of a patient is drilled using a bone cutting tool such as a drill. The drilling of the alveolar bone is a very important procedure, which takes a long time and is difficult to perform.

Now, a brief description will be given of a typical drilling process performed for implant installation. Firstly, the upper part of the alveolar bone is drilled around the toothless site, followed by enlarging of the opening. A surgical guide, fabricated to locate and orient the implant, is mounted to the alveolar bone. While alveolar bone is being watered, the implant site is marked on the surface of the alveolar bone by using an initial drill such as a point drill. The point drill is replaced with a first drill, which in turn enlarges the upper part of the hole while the alveolar bone is being watered. Through such procedures, the hole having a predetermined depth is drilled and becomes gradually enlarged from a small diameter to a larger diameter. The first drill is replaced with a final drill, which in turn enlarges the lower part of the hole while the alveolar bone is being watered. The final drill is then replaced with a tap drill to form threads in the hole while the alveolar bone is being watered. Next, a fixture is coupled into the thread hole using a certain tool, an abutment is fastened to the fixture, and then an artificial tooth is fixed to the abutment using adhesive.

A considerable number of patients have an oral structure which makes it difficult to perform the implant surgery. Particularly, this is the case where only a small amount of bone matrix remains in the posterior area near the maxillary sinus. In this case, the maxillary sinus membrane or, briefly, sinus membrane is lifted to secure a space, a bone graft is placed in the secured space, and a dental implant is embedded in this space. This method is classified into a vertical approach and a lateral approach.

First, the vertical approach (osteotomy) is a method that is used when a bone matrix in a target area for implant surgery is secure to some extent (the thickness of the bone matrix is 4 mm or more), in which method the maxilla is tapped several times with an osteotome (a chisel and a hammer), forming a hole having a diameter from 2 mm to 3 mm, and graft bone material is inserted little by little through the hole. This method has the benefit that a patient has little edema after the surgery because of the narrow target surgery area. However, negatives come from the facts that since the dentist cannot directly see the sinus membrane, he/she has to perform surgery very carefully, checking the membrane with X-ray images, which is time-consuming, thereby prolonging the surgery, and also the patient experiences severe discomfort due to the tapping performed during the surgery.

Next, the lateral approach is a method that is used when a very small amount of bone matrix remains in a target area for implant surgery (the thickness of the bone matrix is 4 mm or less), in which method the maxilla is drilled to form a hole (window) in a lateral side so as to lift the sinus membrane, and bone grafting is carried out through the hole. The method has an advantage in that, since the dentist can lift the sinus membrane and directly view it during the surgery, the membrane is seldom damaged, and further in that, even if damage to the membrane occurs, post-treatment for dealing with the situation is possible, and the desired quantity of bone graft can be laid quickly at one time, so that the processing is implemented quickly. However, the method also has a problem in that the surgery itself is difficult to perform, and a larger valve should be provided, so that severe edema may occur after the surgery. Accordingly, dentists avoid performing such a method in practice.

Recently, in addition to the above methods, a maxillary sinus lift method using a common implant drill and a trephine drill have been recently researched. The method using the implant drill has advantages in that it can minimize the discomfort of patients and is fast to perform. However, at the moment that the maxilla is completely bored by the rotation of the drill blades, the tips of the drill blades can come into contact with the sinus membrane. Since there are no means for preventing the drill blades from contacting the sinus membrane, there is a high risk that the sinus membrane can be torn or damaged by the drill blades. Accordingly, there are demands for solutions that can overcome these problems.

As a conventional approach, Korean Patent No. 0619145, titled 'Implant Drill for Sinus Membrane Lift,' was proposed. The implant drill of the above identified patent is an implant trephine drill form being mounted onto a common dental handpiece. The implant drill has a cutting groove on one end of a tubular body, a central shaft with a shank and a protrusion member elastically positioned in the body so as to protrude and retract in the longitudinal direction in the central portion of the cutting groove of the body end. The protrusion member is inserted into the tubular body and is supported by a spring. Further, the protrusion member has a projection and the tubular body has a projection on the inside wall thereof, so that the projections engage with each other, thereby securing the protrusion member from becoming detached out of the tubular body.

However, in the conventional drill for sinus membrane lift, the protrusion member is integrally provided to the outer circumference of the tubular body, thereby reducing an effective drilling area. Further, since the drill has a sophisticated construction, it is difficult to fabricate the drill or disassemble/assemble the drill for sterilization after surgery.

In particular, efficient drilling is difficult since the tubular body acting as a drilling component is supported by the spring. Further, there is a risk that the sinus membrane may be damaged by a sharp front edge of the protrusion member.

Another conventional approach is to lift the sinus membrane using a piezoelectric device, which uses minute vibration in place of rotation to drill the bone. In this approach, since hard bones can be efficiently drilled but soft tissues are not easily drilled, the maxilla can be drilled without damaging the sinus membrane.

However, this approach has drawbacks in that too much time is spent to drill the bone and there is no measure to control the depth to which the drill is inserted into the maxillary sinus. A thick compact bone takes too much time for drilling, which is somewhat worrisome. Further, there is a risk that a surgeon may apply an excessive force so excessively that the drill can be pushed into the maxillary sinus, thereby tearing or damaging the sinus membrane.

DISCLOSURE

Technical Problem

The present invention has been made to solve the foregoing problems with the prior art, and therefore embodiments of the present invention provide a drill for implant surgeries, which can stably and rapidly drill the maxilla for implant installation without causing damage to the sinus membrane in order to facilitate a procedure, minimize the discomfort of a patient, and reduce procedure time. The drill is dedicated to the maxillary sinus. The sinus membrane is not drilled even if the drill contacts the sinus membrane while drilling at a high speed. Further, the drill has a safety means that can prevent the drill from being excessively inserted into the maxillary sinus and thus damaging the sinus membrane.

Technical Solution

According to an aspect of the present invention, the drill for sinus membrane lift may include a contact surface for making in face contact with sinus membrane, the contact surface having a curved periphery; a bone-maintaining area connected to the contact surface to store and discharge drilled bone fragments. The bone-maintaining area includes a first inside wall and a second inside wall connected to the first inside wall, the first inside wall oriented in a drilling direction, and the second inside wall opposite the first inside wall. The first inside wall has a drilling surface and is formed higher than the second inside wall so that the drilling surface is exposed in the drilling direction.

In an exemplary embodiment of the present invention, the contact surface is formed on a head provided on an elongated body, the head having a diameter equal to, enlarged or reduced respective to that of the body.

In another exemplary embodiment of the present invention, the bone-maintaining area includes an axis.

In a further exemplary embodiment of the present invention, the body has a shank as an integral part thereof, the shank selectively connected to a dental handpiece.

In another exemplary embodiment of the present invention, the body includes a cylindrical fitting part having an enlarged diameter and a disk-shaped retreat stop plate extending from one portion of the fitting part with an enlarged diameter. The drill may further include a hollow tubular stopper selectively provided on the fitting part, wherein the stopper limits a depth to which the head drills the maxilla.

In another exemplary embodiment of the present invention, the bone-maintaining area is formed of a through hole extending from the head to a portion of the body.

In a further exemplary embodiment of the present invention, the bone-maintaining area is formed of a concave recess dug from the head to a portion of the body.

In a further exemplary embodiment of the present invention, the bone-maintaining area including the first and second inside walls has a predetermined configuration, which is a circle, a triangle or a polygon as seen from the contact surface.

In another exemplary embodiment of the present invention, the drill may include from one to three of the bone-maintaining areas, which are arranged around an axis of the contact surface.

In a further exemplary embodiment of the present invention, the contact surface is one selected from the group consisting of a flat surface, a bulging curved surface and an inclined surface formed around an axis to extend toward the outer circumference at a downward slope.

In another exemplary embodiment of the present invention, the bone-maintaining area runs parallel to or enlarges from the contact surface toward a rear part thereof in order to gradually discharge the drilled bone fragments.

In a further exemplary embodiment of the present invention, the drill may include at least two of the bone-maintaining areas, wherein one of the bone-maintaining areas includes an axis.

In yet another exemplary embodiment of the present invention, the stopper may include an elastic part including a plurality of elastic pieces for being elastically fitted into the fitting part and slits extending in a longitudinal direction thereof, wherein the slits are spaced from one another at a constant interval to separate the elastic pieces from each another; a support tube extending from the elastic part; and a contact tube extending from the support tube, wherein the contact tube has a predetermined diameter to receive the head therein.

The above and other objects, features and other advantages of the present invention will be more clearly understood from the following detailed description taken in conjunction with the accompanying drawings. Herein, the terminologies or words used in the description and the claims of the present invention should not be interpreted as being limited merely to common and dictionary meanings. On the contrary, they should be interpreted based on the meanings and concepts of the present invention in compliance with the scope of the present invention on the basis of the principle that the inventor(s) can appropriately define the terms in order to describe the present invention in the best way.

Advantageous Effects

In the drill for sinus membrane lift of the present invention, the front end of the head is configured to come into face contact with the sinus membrane over a wide area in order to prevent the sinus membrane from being torn or damaged even if the head completely penetrates the maxilla and contacts the sinus membrane. As a result, the safety of the procedure can be better ensured and the procedure time can be greatly reduced.

Moreover, the depth of drilling can be limited by the stopper fitted onto the outer circumference of the body, thereby ensuring the safety of the procedure. The simple structure makes use thereof and management easier and enables mass production so that products can be standardized and economically distributed.

MAJOR REFERENCE NUMERALS OF DRAWINGS

Figure 1:
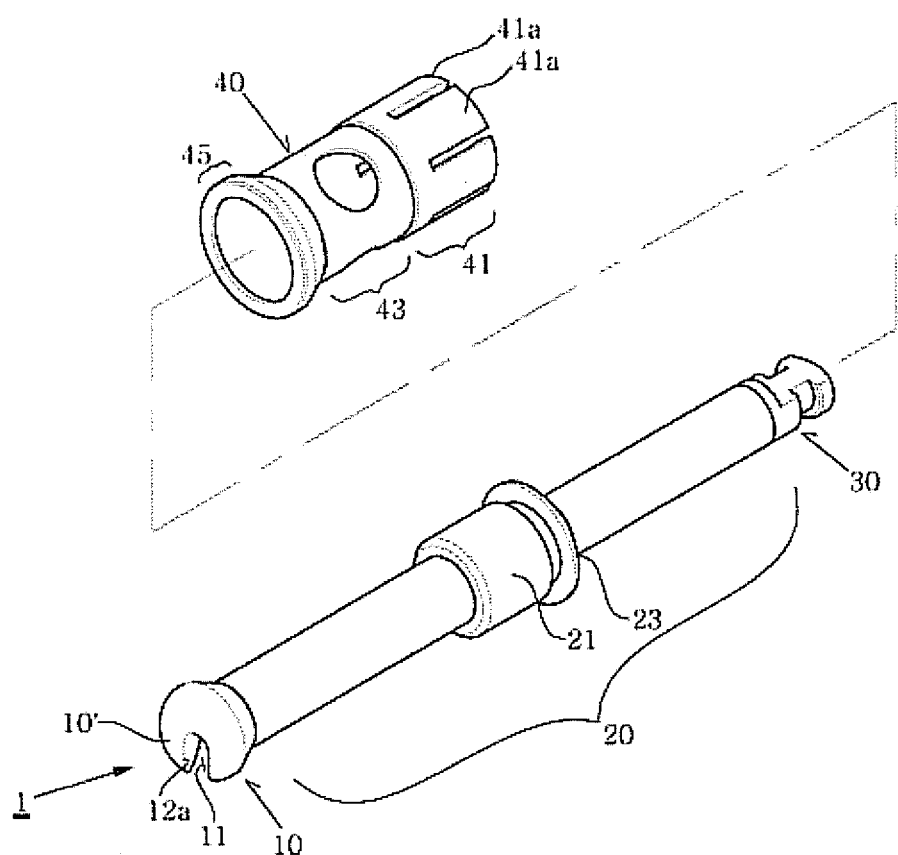
FIGS. 1 to 6 illustrate a drill for sinus membrane lift according to a first embodiment of the present invention.

1: drill for sinus membrane lift
10: head 10': contact surface
11: bone-maintaining area 12: first inside wall
12a: drilling surface 13: second inside wall
20: body 21: fitting part
23: retreat stop plate 30: shank
40: stopper

MODE FOR INVENTION

Hereinafter, a drill for sinus membrane lift of the present invention will be described with reference to the accompanying drawings.

Reference should now be made to the drawings, in which the same reference numerals are used throughout the different drawings to designate the same or similar components. In the following description, well-known functions or constructions by a person skilled in the art are not described in detail when such unnecessary detail would obscure the gist of the present invention.

Figure 2:
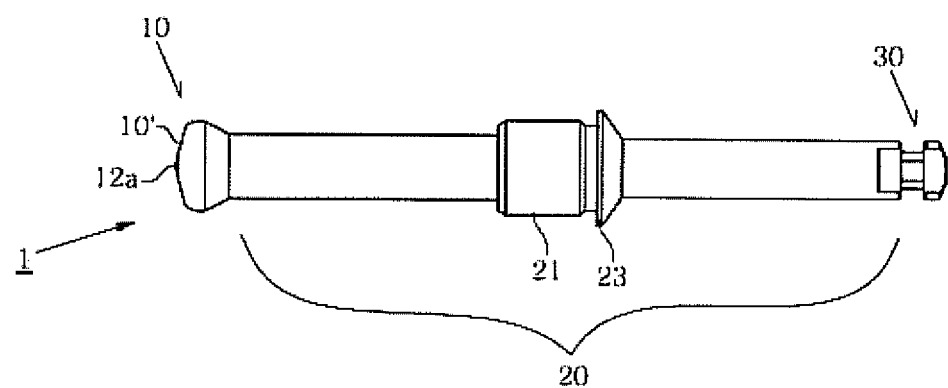
Figure 3:
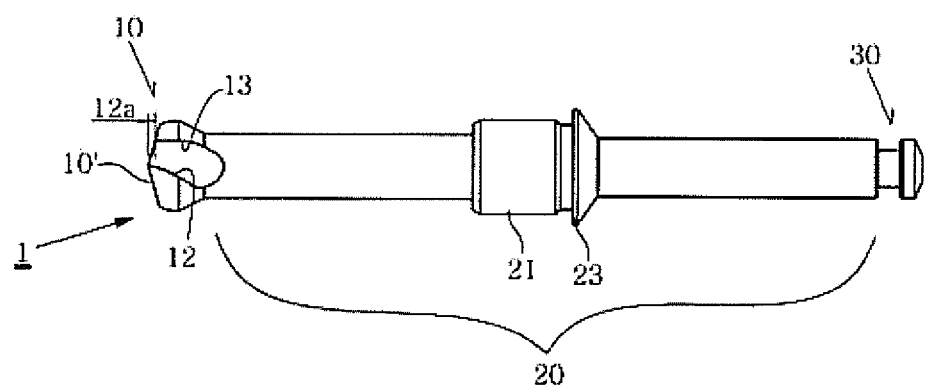
Figure 4:
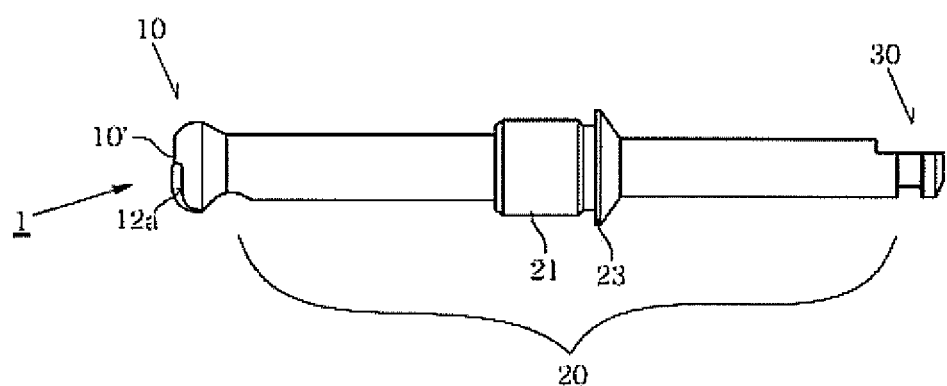
Figure 5:
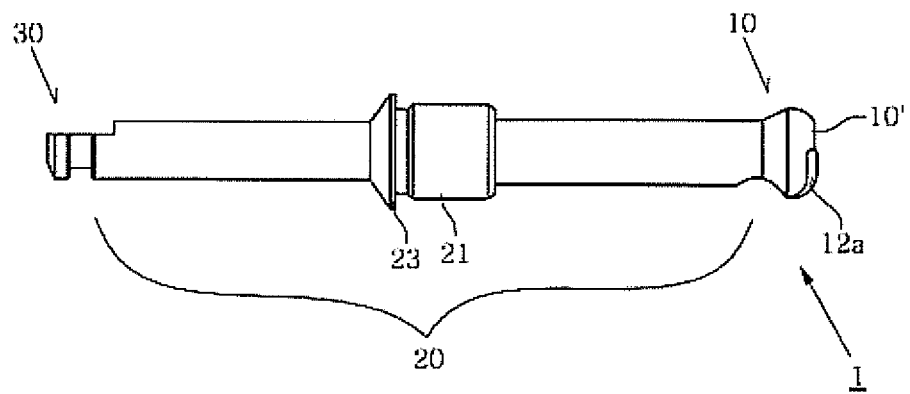
Figure 6:
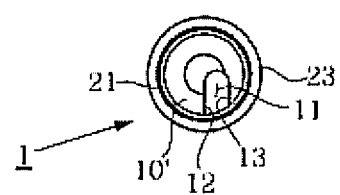

FIGS. 1 to 6 illustrate a drill for sinus membrane lift according to a first embodiment of the present invention, in which: FIG. 1 is a perspective view illustrating the first embodiment; FIG. 2 is a plan view of FIG. 1 as viewed from above; FIG. 3 is a front elevational view; FIG. 4 is a bottom view of FIG. 1 viewed from below; FIG. 5 is a rear elevational view; and FIG. 6 is a left elevational view of FIG. 1, which is seen from the left in order to explain a contact surface.

As shown in these drawings, a drill for sinus membrane lift 1 includes a generally cylindrical tubular body 20 having a predetermined length, a head 10 provided integrally at one end of the body 20 so as to act as a drilling end for the maxilla, and a shank 30 selectively connecting a dental handpiece to the other end of the body 20 opposite the head 10.

This construction of the drill for sinus membrane lift 1 is somewhat similar to the known construction of the conventional drill for sinus membrane lift. In the head 10 of the present invention, however, a drilling surface 12a is formed so as to protect the sinus membrane in an upper portion of the maxilla from being perforated or damaged, and a bone-maintaining area 11 is formed to include the drilling surface 12a and to contain and discharge bone fragments, which are cut off from the maxilla. Further, a stopper is optionally provided on the body 20 so as to limit the depth of a cut in the bone formed by the head 10.

The head 10 is formed with a diameter the same as the body 20, or with a reduced or enlarged size. The periphery of the head 10 is machined to be round, that is, formed as a curved surface.

The head 10 can be constructed with a flat surface formed by machining, a bulging curved surface, or a conical surface formed around the altitude so as to extend toward the directrix at a slow downward slope, so that a large surface of the head 10 can come into contact with the sinus membrane when a contact surface 10' is brought into contact with the sinus membrane.

Further, the contact surface 10' is formed with one bone-maintaining area 11, which stores and discharges bone fragments. The bone-maintaining area 11 is defined by connecting a first inside wall 12, oriented in a drilling direction of the bone, to a second inside wall 13 opposite the first inside wall 12. In this embodiment, the first and second inside walls 12 and 13 are connected to each other and form a smooth curved surface.

The first inside wall 12 is formed higher than the second inside wall 13, so that the drilling surface 12a is exposed in the drilling direction. The drilling surface 12a of this configuration acts to drill the maxilla when rotated in a forward direction. The bone fragments drilled like this will first fill a predetermined area of the bone-maintaining area 11 and then be discharged to outside the bone-maintaining area 11.

The bone-maintaining area 11 is formed with a concave portion, which uniformly extends from the head 10 to a portion of the bottom plate. As shown in the drawings, the bone-maintaining area 11 is open to the front end and the side surface of the head 10 and to the side surface of the body 20. Further, the front-end groove area of the bone-maintaining area 11 preferably includes the central axis passing therethrough, so that the bone can be stably drilled around the axis when the drill is being rotated.

The body 20 is connected to the bone-maintaining area 11 together with the head 10, and has a cylindrical fitting part 21 and retreat stop plate 23. The cylindrical fitting part 21 is formed with an enlarged diameter on the outer circumference of the body 20 behind the bone-maintaining area 11. The retreat stop plate 23 is provided on a rear portion of the coupling part 21 to prevent a stopper 40, which will be described later, from retreating.

The stopper 40 is a hollow tubular member, which is designed to limit a depth to which the head 10 drills the maxilla. The stopper 40 includes an elastic part 41, which is a tubular arrangement of a plurality of elastic pieces 41a there for being elastically fitted into the fitting part 21, a support tube 43 extending from one end of the elastic part 41 and a contact tube 45 extending from one end of the support tube 43. The support tube 43 has a predetermined diameter to smoothly receive the body 20 therein, and the contact tube 45 has an enlarged diameter to receive the head 10.

In the elastic part 41, the elastic pieces 41a are formed by slits, which extend along the longitudinal direction at a constant interval. The elastic part 41 has a predetermined inside diameter to allow press-fitting onto the fitting part 21.

The stopper 40 can be prepared at a variety of lengths according to the depth of the maxilla to be drilled. The contact tube 45 limits the degree of exposure of the head 10. That is, when the head 10 drills the maxilla to a predetermined depth, the head 45 contacts the maxilla so that the head 10 cannot advance any further. In this manner, the contact tube 45 limits the depth of drilling the maxilla.

When the drill for sinus membrane lift constructed as above according to this embodiment of the present invention is rotated in the forward direction, the drilling surface 12a will drill the maxilla, and bone fragments drilled thereby will fill in the bone-maintaining area 11 connected to the drilling surface 12*a*. When a predetermined amount of the bone fragments are filled in the bone-maintaining area 11, they will be moved and discharged toward the body 20.

In sequence, when the contact surface 10' of the head 10 reams the maxilla, one smooth surface, made of the contact surface 10' and the maintained bone fragments, will come into face contact with the sinus membrane at a wide area so as to protect the sinus membrane from damage.

Figure 7:
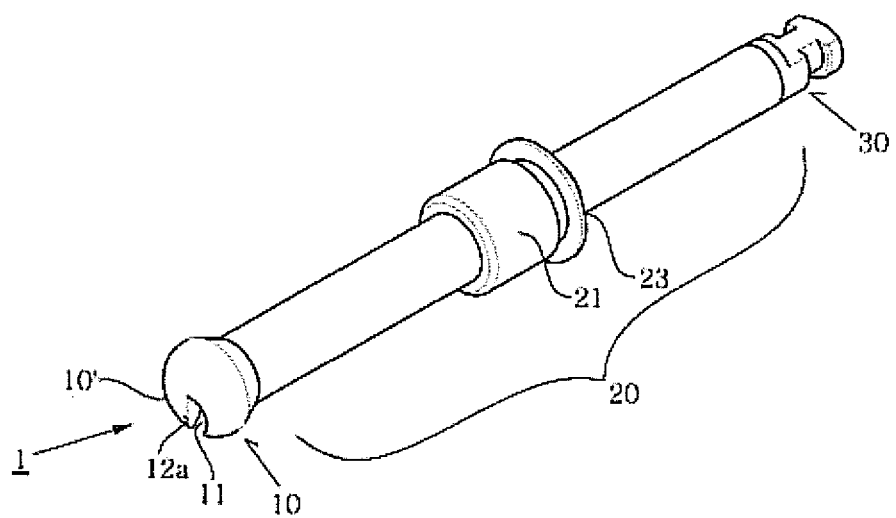
FIGS. 7 to 12 illustrate a drill for sinus membrane lift according to a second embodiment of the present invention.
Figure 8:
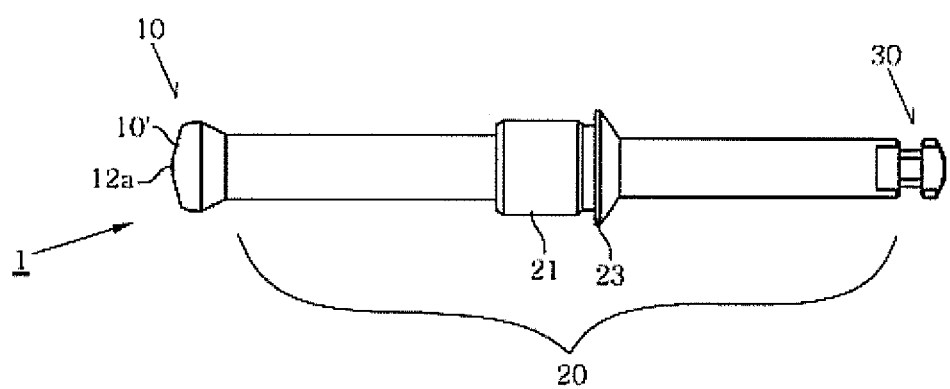
Figure 9:
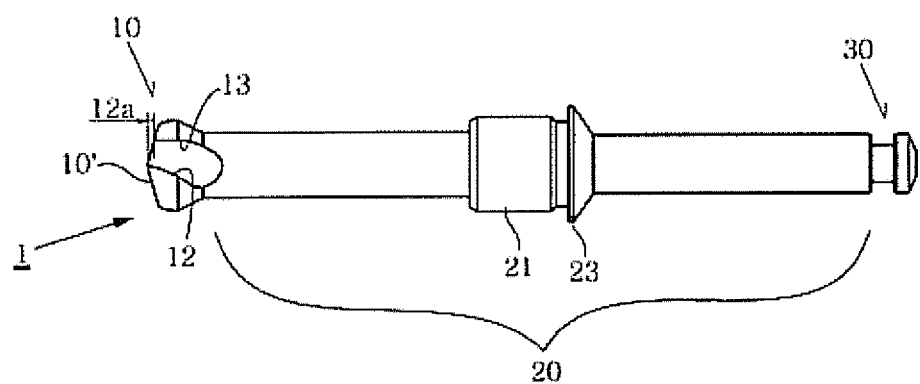
Figure 10:
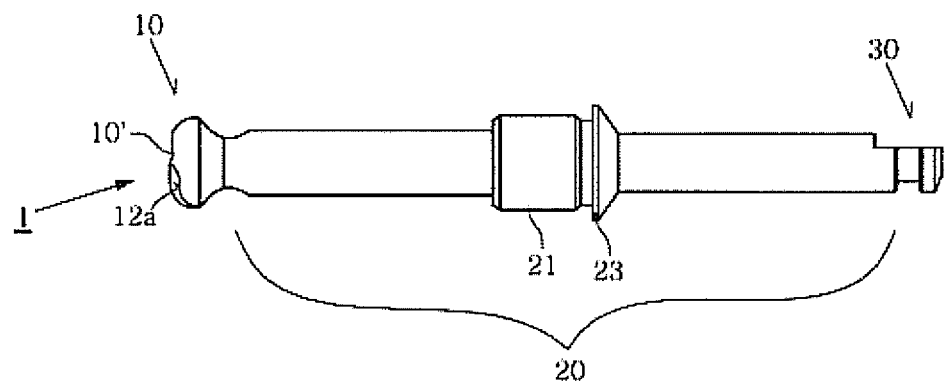
Figure 11:
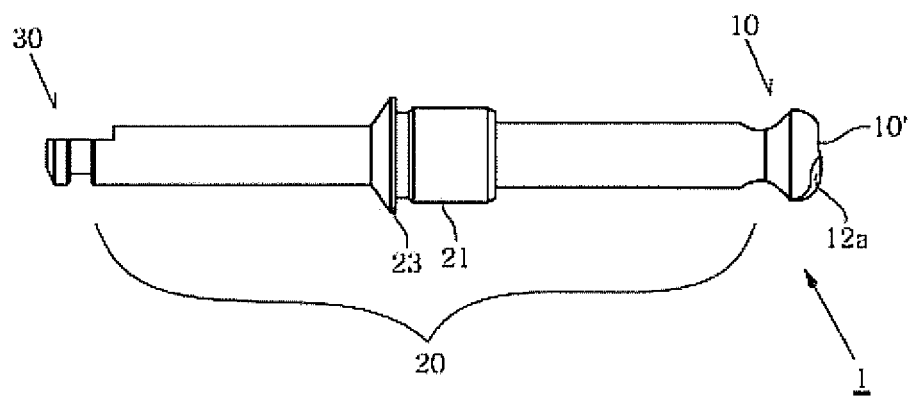
Figure 12:
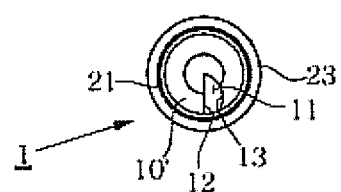

FIGS. 7 to 12 illustrate a drill for sinus membrane lift according to a second embodiment of the present invention, in which FIG. 7 is a perspective view illustrating the first second embodiment, FIG. 8 is a plan view of FIG. 7, which is viewed from above, FIG. 9 is a front elevational view, FIG. 10 is a bottom view of FIG. 7, which is viewed from below, FIG. 11 is a rear elevational view, and FIG. 12 is a left elevational view of FIG. 7, which is seen from the left in order to explain a contact surface.

The drill for sinus membrane lift 1 of this embodiment has a similar construction to that of the first embodiment as described above. Herein, the same components will be designated with the same reference numerals and will not be described in detail.

As shown in the drawings, characteristic features of this embodiment are that the first inside wall 12 and the second inside wall 13 are directly connected to each other unlike in the first embodiment. Specifically, the first and second inside walls 12 and 13 run parallel to each other and then are connected to each other at an acute angle.

Figure 13:
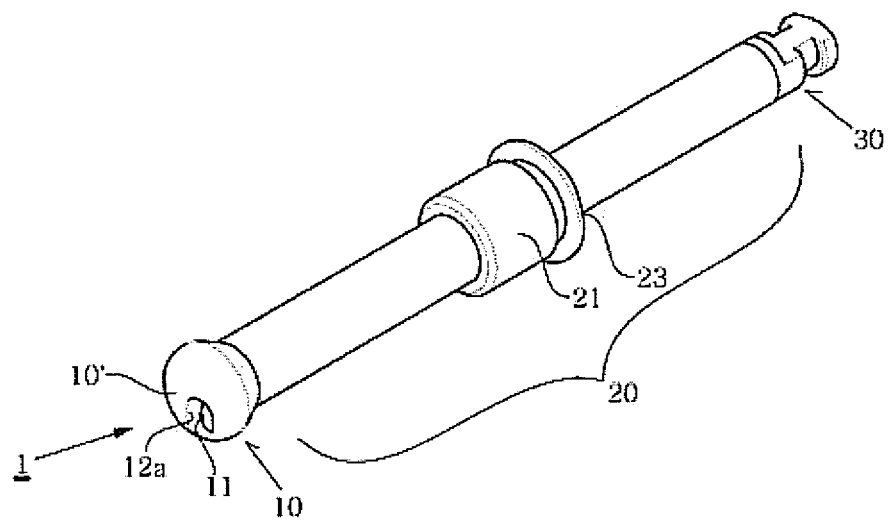
FIGS. 13 to 18 illustrate a drill for sinus membrane lift according to a third embodiment of the present invention.
Figure 14:
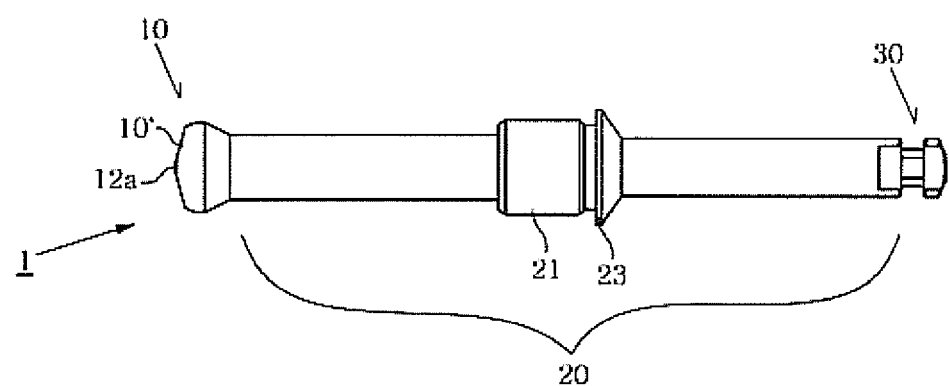
Figure 15:
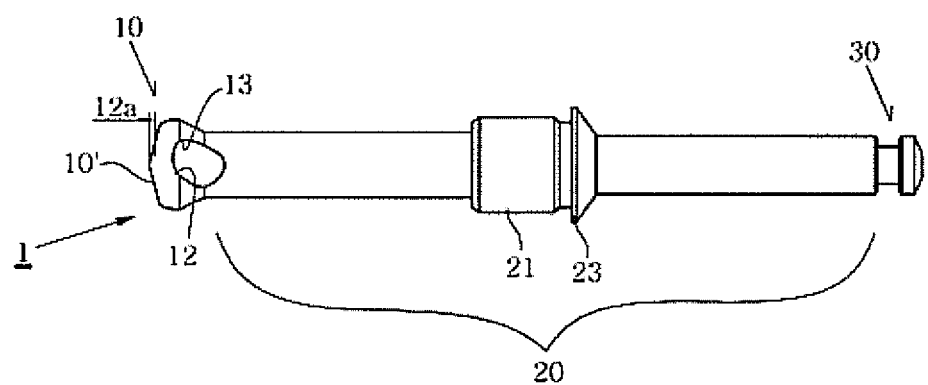
Figure 16:
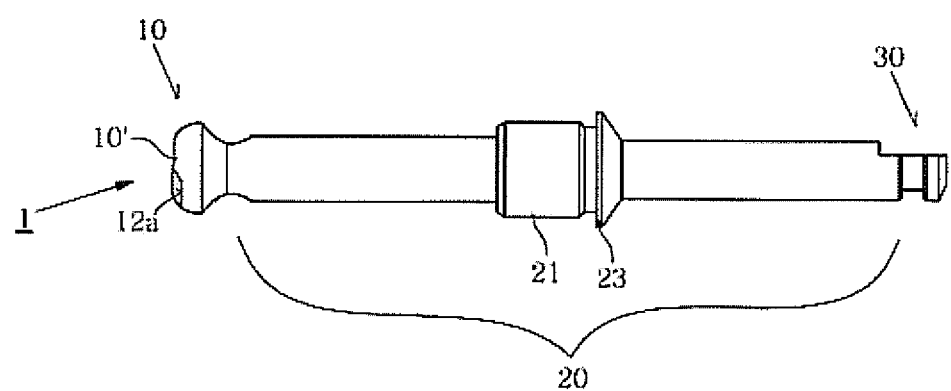
Figure 17:
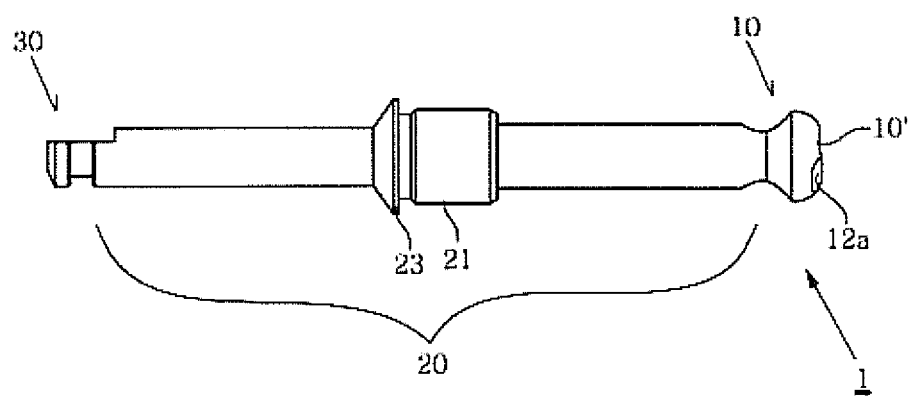
Figure 18:
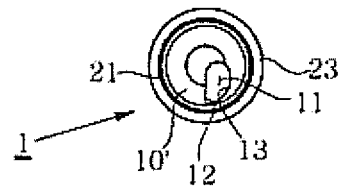

FIGS. 13 to 18 illustrate a drill for sinus membrane lift according to a third embodiment of the present invention, which is designed to maintain bone fragments as well as minimize any perforation of the membrane. In these drawings, FIG. 13 is a perspective view illustrating the third embodiment, FIG. 14 is a plan view of FIG. 13 as viewed from above, FIG. 15 is a front elevational view, FIG. 16 is a bottom view of FIG. 13 viewed from below, FIG. 17 is a rear elevational view, and FIG. 18 is a left elevational view of FIG. 13, which is seen from the left in order to explain a contact surface.

The drill for sinus membrane lift 1 of this embodiment has a similar construction to that of the first embodiment as described above. While the bone-maintaining area 11 was proposed to be in the form of a concave cavity or recess in the first embodiment, it is proposed to be in the form of a through hole in this embodiment. This provides a safer configuration for minimizing the damage of the sinus membrane. It should also be appreciated that the drilling surface of an external connecting part be formed in the upper part at an acute angle in order to enhance the drilling force of the external connecting part.

Figure 19:
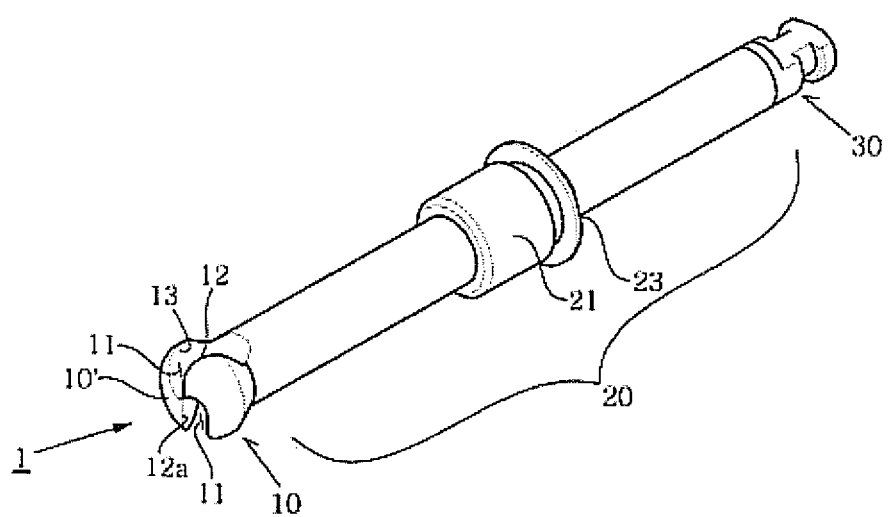
FIGS. 19 to 24 illustrate a drill for sinus membrane lift according to a fourth embodiment of the present invention.
Figure 20:
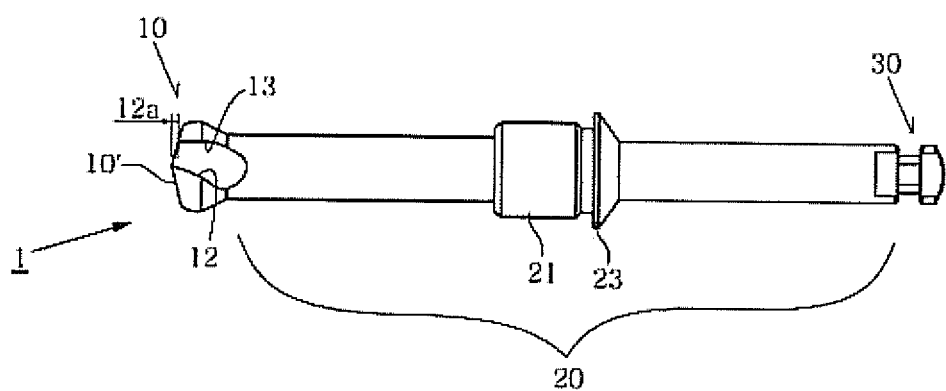
Figure 21:
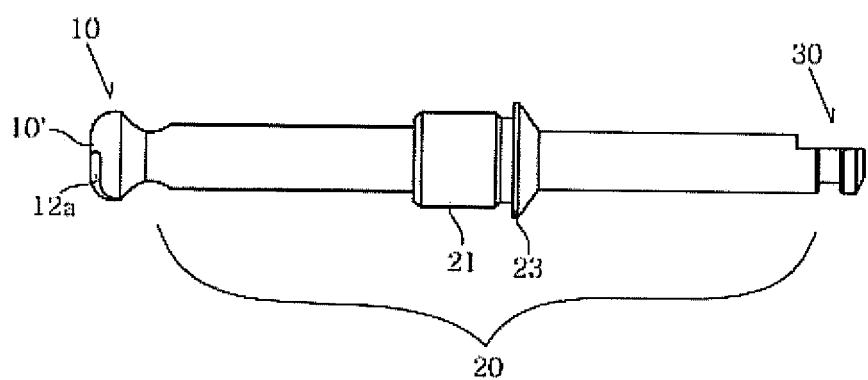
Figure 22:
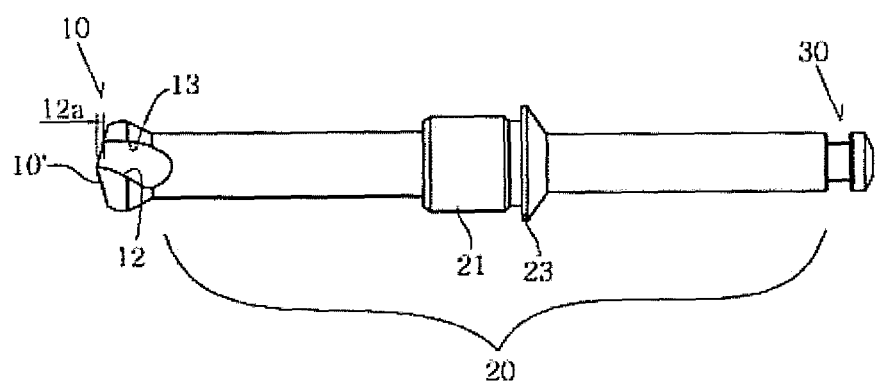
Figure 23:
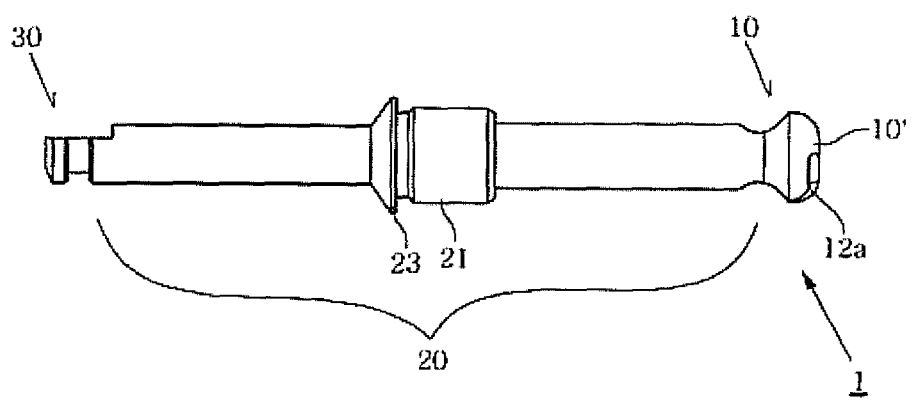
Figure 24:
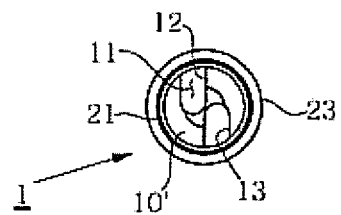

FIGS. 19 to 24 illustrate a drill for sinus membrane lift according to a fourth embodiment of the present invention, in which FIG. 19 is a perspective view illustrating the fourth embodiment, FIG. 20 is a plan view of FIG. 19, which is viewed from above, FIG. 21 is a front elevational view, FIG. 22 is a bottom view of FIG. 19, which is viewed from below, FIG. 23 is a rear elevational view, and FIG. 24 is a left elevational view of FIG. 19, which is seen from the left in order to explain a contact surface.

The drill for sinus membrane lift 1 of this embodiment has a similar construction to that of the first embodiment as described above. Herein, the same components will be designated with the same reference numerals and will not be described in detail.

As shown in the drawings, this embodiment proposes two bone-maintaining areas 11 as characteristic features, which are spaced apart from one another at a constant interval.

The bone-maintaining areas 11 are connected to each other by a smoothly curved surface. In each of the bone-maintaining areas 11, the first inside wall 12 is arranged opposite the second inside wall 13.

In a pair of the bone-maintaining areas 11, one of the two bone-maintaining areas can preferably include the central axis so as to allow uniformly drilling of the maxilla.

Figure 25:
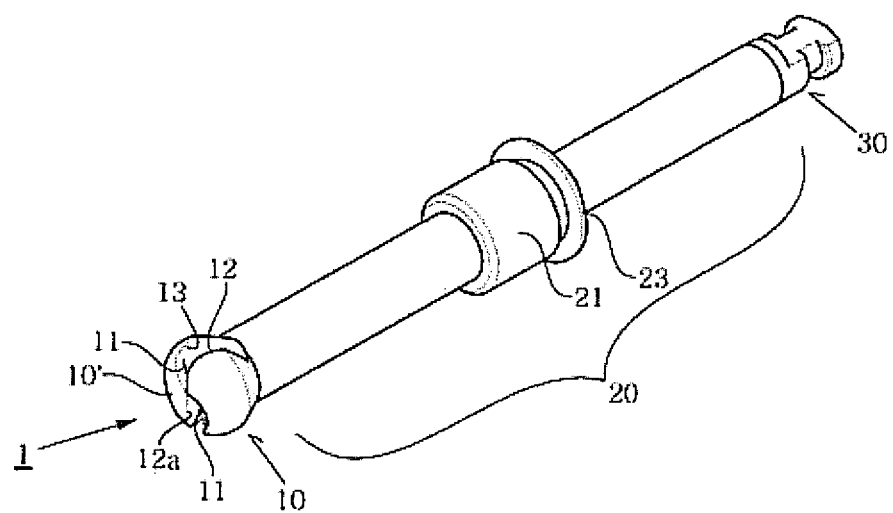
FIGS. 25 to 30 illustrate a drill for sinus membrane lift according to a fifth embodiment of the present invention.
Figure 26:
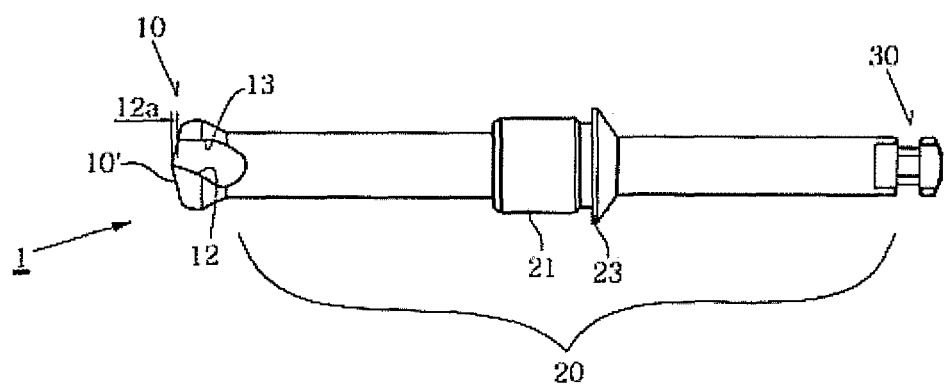
Figure 27:
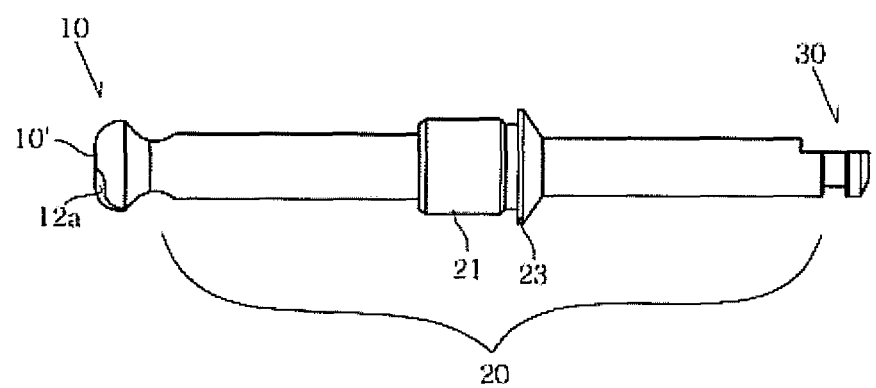
Figure 28:
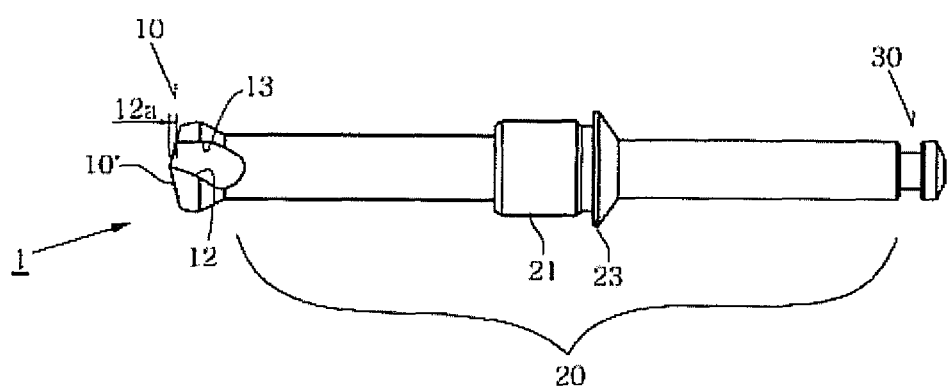
Figure 29:
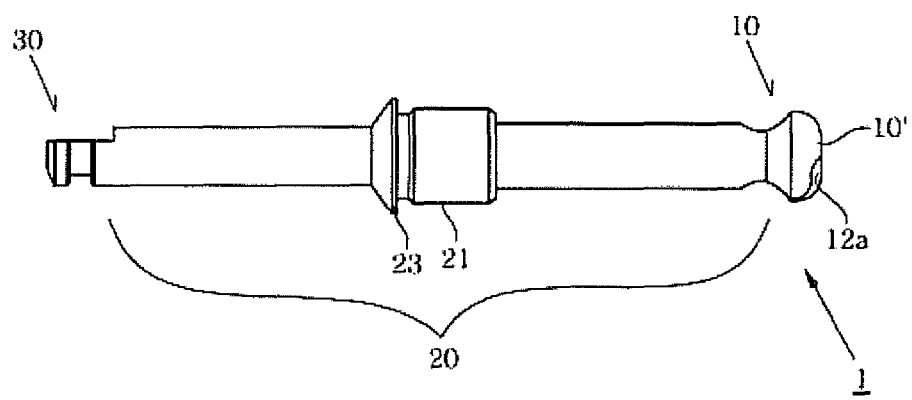
Figure 30:
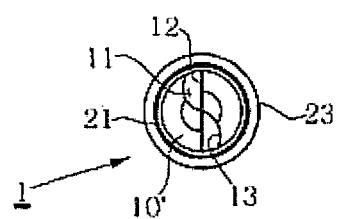

FIGS. 25 to 30 illustrate a drill for sinus membrane lift according to a fifth embodiment of the present invention, in which FIG. 25 is a perspective view illustrating the fifth embodiment, FIG. 26 is a plan view of FIG. 25 as viewed from above, FIG. 27 is a front elevational view, FIG. 28 is a bottom view of FIG. 25, which is viewed from below, FIG. 29 is a rear elevational view, and FIG. 30 is a left elevational view of FIG. 25, which is seen from the left in order to explain a contact surface.

The drill for sinus membrane lift 1 of this embodiment has a similar construction to that of the second embodiment as described above. Herein, the same components will be designated with the same reference numerals and will not be described in detail.

As shown in the drawings, this embodiment proposes two bone-maintaining areas 11 as characteristic features, which are spaced apart from each other with a uniform interval.

In the bone-maintaining areas 11, the first inside wall 12 and the second inside wall 13 are arranged opposite each other and are connected to each other at an acute angle.

Further, in a pair of the bone-maintaining areas 11, one of the two bone-maintaining areas can preferably include the central axis so as to effectively drill the maxilla.

Figure 31:
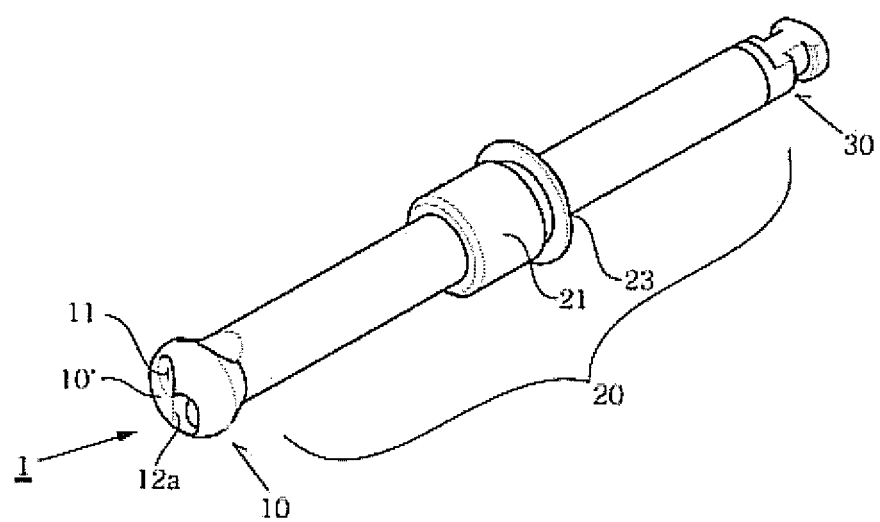
FIGS. 31 to 36 illustrate a drill for sinus membrane lift according to a sixth embodiment of the present invention.
Figure 32:
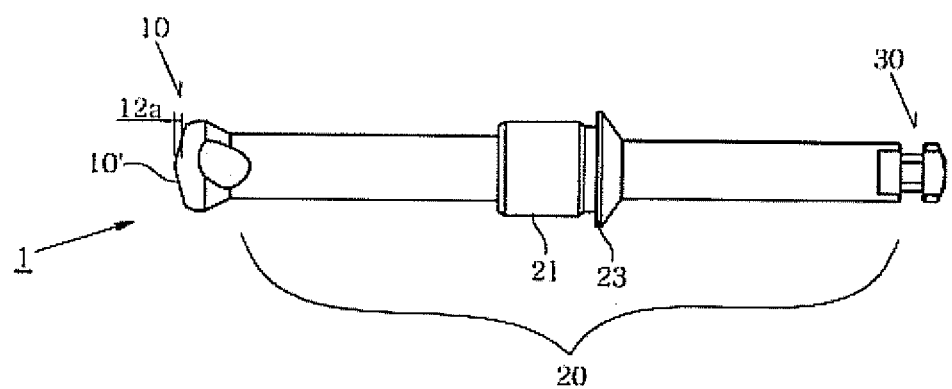
Figure 33:
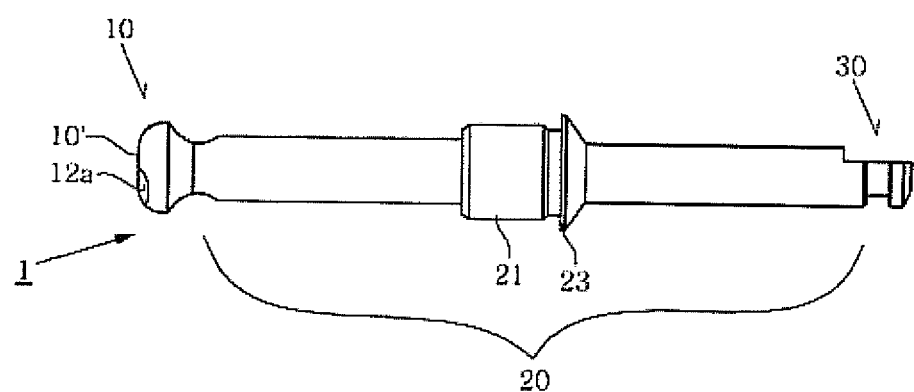
Figure 34:
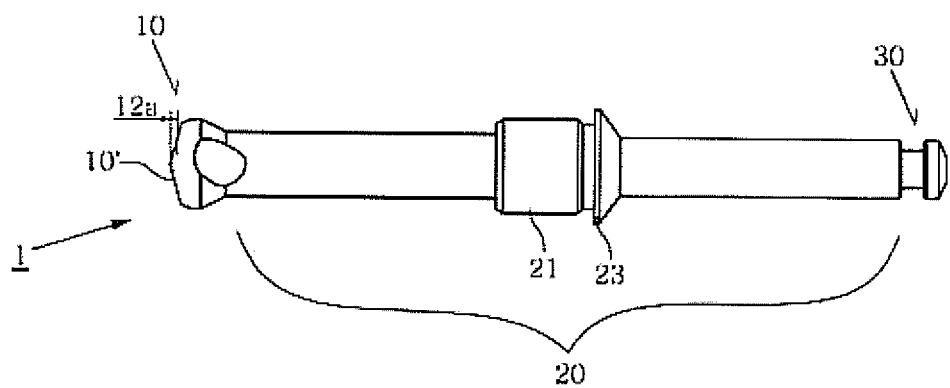
Figure 35:
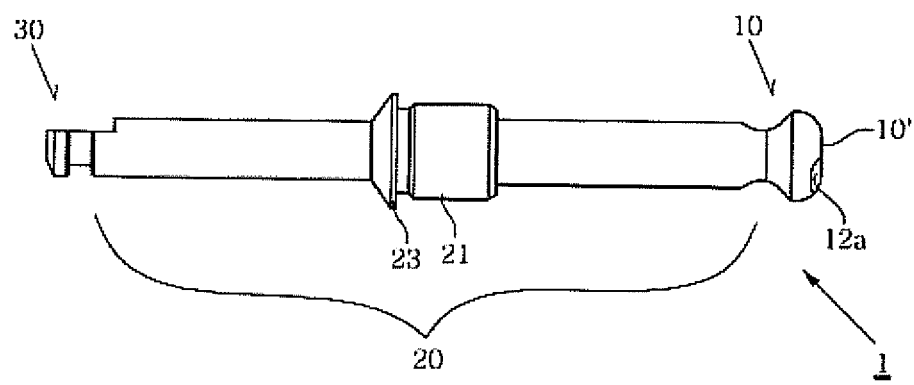
Figure 36:
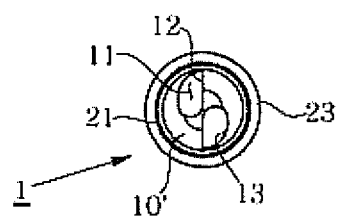

FIGS. 31 to 36 illustrate a drill for sinus membrane lift according to a sixth embodiment of the present invention, in which FIG. 31 is a perspective view illustrating the sixth embodiment, FIG. 32 is a plan view of FIG. 31, which is viewed from above, FIG. 33 is a front elevational view, FIG. 34 is a bottom view of FIG. 31, which is viewed from below, FIG. 35 is a rear elevational view, and FIG. 36 is a left elevational view of FIG. 31, which is seen from the left in order to explain a contact surface.

The drill for sinus membrane lift 1 of this embodiment has a similar construction to that of the third embodiment as described above. Herein, the same components will be designated with the same reference numerals and will not be described in detail.

While the drill for sinus membrane lift 1 as the characteristic feature of this embodiment is similar to that of the third embodiment, this embodiment proposes two bone-maintaining areas 11 to be spaced apart from each other by a uniform interval as shown in the drawings.

The respective bone-maintaining areas 11 are provided in the form of through holes, and one of the bone-maintaining areas 11 can preferably include the central axis so as to allow uniform and effective drilling of the maxilla.

While the present invention has been described by way of example as being applied to the maxillary sinus, this is not intended to limit the present invention. Rather, the drill of the present invention can be applied to various parts such as a mandibular posterior area. It should also be understood that those skilled in the art can change or modify the embodiments in various forms without departing from the scope and spirit of the present invention. Accordingly, all the changes and modifications shall be embraced by the scope of the present invention as defined the appended claims.

What is claimed is:

1. A drill for sinus membrane lift, comprising:
   an elongated body extending longitudinally along a longitudinal center axis thereof;
   a head disposed at a distal end of the elongated body and having a distal contact surface for coming in face contact with a sinus membrane, the distal contact surface having a curved or generally convex surface contour disposed symmetrically about a central axis of the head, which axis is coaxial with the longitudinal center axis of the elongated body; and
   a bone-maintaining area connected to the distal contact surface and shaped in a groove extending in a longitudinal direction of the elongated body to store and discharge drilled bone fragments,
   wherein the groove of the bone-maintaining area includes a first inside wall and a second inside wall connected to the first inside wall, the first inside wall oriented in a drilling direction, and the second inside wall opposite the first inside wall,
   wherein the central axis of the head is passing through a front-end groove area of the bone-maintaining area, and the first inside wall has a drilling surface and is formed higher than the second inside wall so that the drilling surface is exposed in the drilling direction,
   wherein the groove of the bone-maintaining area extends from the head to a portion of the elongated body.

2. The drill for sinus membrane lift according to claim 1, wherein the body has a shank as an integral part thereof, the shank selectively connected to a dental handpiece.

3. The drill for sinus membrane lift according to claim 1, wherein the body includes a cylindrical fitting part having an enlarged diameter; and a disk-shaped retreat stop plate extending from one portion of the fitting part with an enlarged diameter, the drill further comprising a hollow tubular stopper selectively provided on the fitting part, wherein the stopper limits a depth to which the head drills a maxilla.

4. The drill for sinus membrane lift according to claim 3, wherein the stopper includes:
   an elastic part including a plurality of elastic pieces for being elastically fitted into the fitting part and slits extending in a longitudinal direction thereof, wherein the slits are spaced from one another at a constant interval to separate the elastic pieces from one another;
   a support tube extending from the elastic part; and
   a contact tube extending from the support tube, wherein the contact tube has a predetermined diameter to receive the head therein.

5. The drill for sinus membrane lift according to claim 1, wherein the bone-maintaining area including the first and second inside walls has a predetermined configuration which includes a circular or curved surface as seen from the distal contact surface.

6. The drill for sinus membrane lift according to claim 1, comprising from one to three of the bone-maintaining areas, which are arranged around the central axis of the distal contact surface.

7. The drill for sinus membrane lift according to claim 1, wherein the distal contact surface includes a flat surface, a bulging curved surface, or an inclined surface formed around the central axis to extend towards an outer circumference at a downward slope.

8. The drill for sinus membrane lift according to claim 1, wherein the bone-maintaining area runs parallel to or enlarges from the distal contact surface toward a rear part thereof in order to gradually discharge drilled bone fragments.

9. The drill for sinus membrane lift according to claim 1, comprising at least two of the bone-maintaining areas, wherein one of the bone-maintaining areas includes the central axis of the head passing through the front-end groove area of the bone-maintaining area.

10. A drill for sinus membrane lift, comprising:
    an elongated body extending longitudinally along a longitudinal center axis thereof;
    a head disposed at a distal end of the elongated body and having a distal contact surface for coming in face contact with a sinus membrane, the distal contact surface having a curved or generally convex surface contour disposed symmetrically about a central axis of the head, which axis is coaxial with the longitudinal center axis of the elongated body; and
    a bone-maintaining area connected to the distal contact surface and shaped in a through hole extending in a longitudinal direction of the elongated body from the head to a groove portion of the elongated body to store and discharge drilled bone fragments,
    wherein the through hole of the bone-maintaining area includes a first inside wall portion and a second inside wall portion connected to the first inside wall portion, the first inside wall portion oriented in a drilling direction, and the second inside wall portion opposite the first inside wall portion,
    wherein the central axis of the head is passing through a front-end groove hole area of the bone-maintaining area, and the first inside wall portion has a drilling surface and is formed higher than the second inside wall portion so that the drilling surface is exposed in the drilling direction,
    wherein the through hole of the bone-maintaining area extends from the head and communicates with the groove portion of the elongated body.

* * * * *